United States Patent
Blommel et al.

(10) Patent No.: US 9,873,643 B2
(45) Date of Patent: *Jan. 23, 2018

(54) DEHYDROGENATION OF ALKANOLS TO INCREASE YIELD OF AROMATICS

(71) Applicant: Virent, Inc., Madison, WI (US)

(72) Inventors: Paul G. Blommel, Oregon, WI (US);
Li Yuan, Madison, WI (US); Matthew Van Straten, Madison, WI (US);
Warren Lyman, Madison, WI (US);
Randy D. Cortright, Madison, WI (US)

(73) Assignee: Virent, Inc., Madison, WI (US)

( * ) Notice: Subject to any disclaimer, the term of this patent is extended or adjusted under 35 U.S.C. 154(b) by 235 days.

This patent is subject to a terminal disclaimer.

(21) Appl. No.: 14/583,312

(22) Filed: Dec. 26, 2014

(65) Prior Publication Data
US 2015/0133705 A1 May 14, 2015

Related U.S. Application Data

(63) Continuation of application No. 13/900,400, filed on May 22, 2013, now Pat. No. 8,962,902, which is a
(Continued)

(51) Int. Cl.
*C07C 1/22* (2006.01)
*C07C 1/207* (2006.01)
(Continued)

(52) U.S. Cl.
CPC ........... *C07C 1/22* (2013.01); *B01J 21/04* (2013.01); *B01J 23/462* (2013.01); *B01J 23/50* (2013.01); *B01J 23/72* (2013.01); *B01J 23/75* (2013.01); *B01J 23/80* (2013.01); *B01J 23/868* (2013.01); *B01J 29/061* (2013.01); *B01J 29/44* (2013.01);
(Continued)

(58) Field of Classification Search
None
See application file for complete search history.

(56) References Cited

U.S. PATENT DOCUMENTS 1,977,750 A 10/1934 Young
2,220,624 A 11/1940 Sherrard et al.
(Continued)

FOREIGN PATENT DOCUMENTS

GB 1446522 8/1976
GB 1526461 9/1978
JP 57-102835 6/1982

OTHER PUBLICATIONS

Zhang et al., Catalytic conversion of biomass-derived feedstocks into olefins and aromatics with ZSM-5: the hydrogen to carbon effective ratio, Energy & Environmental Science, The Royal Society of Chemistry, 2011, 4, 2297-2307.*
(Continued)

*Primary Examiner* — Philip Louie
(74) *Attorney, Agent, or Firm* — Quarles & Brady LLP

(57) ABSTRACT

The present invention provides methods, reactor systems, and catalysts for increasing the yield of aromatic hydrocarbons produced while converting alkanols to hydrocarbons. The invention includes methods of using catalysts to increase the yield of benzene, toluene, and mixed xylenes in the hydrocarbon product.

21 Claims, 4 Drawing Sheets

Related U.S. Application Data continuation-in-part of application No. 13/304,052, filed on Nov. 23, 2011, now Pat. No. 8,969,640.

(51) Int. Cl.

| | | |
|---|---|---|
| *C01B 3/22* | (2006.01) | |
| *C10G 3/00* | (2006.01) | |
| *B01J 37/08* | (2006.01) | |
| *B01J 21/04* | (2006.01) | |
| *B01J 23/46* | (2006.01) | |
| *B01J 23/50* | (2006.01) | |
| *B01J 23/72* | (2006.01) | |
| *B01J 23/75* | (2006.01) | |
| *B01J 23/80* | (2006.01) | |
| *B01J 23/86* | (2006.01) | |
| *B01J 29/06* | (2006.01) | |
| *B01J 29/44* | (2006.01) | |
| *B01J 29/46* | (2006.01) | |
| *B01J 29/48* | (2006.01) | |
| *B01J 35/02* | (2006.01) | |
| *B01J 37/02* | (2006.01) | |
| *C07C 45/38* | (2006.01) | |
| *C07C 45/00* | (2006.01) | |
| *C07C 51/00* | (2006.01) | |
| *C07C 67/00* | (2006.01) | |
| *B01J 23/00* | (2006.01) | |
| *B01J 25/00* | (2006.01) | |

(52) U.S. Cl.
CPC ............ *B01J 29/46* (2013.01); *B01J 29/48* (2013.01); *B01J 35/023* (2013.01); *B01J 37/0201* (2013.01); *B01J 37/08* (2013.01); *C01B 3/22* (2013.01); *C07C 1/2078* (2013.01); *C07C 45/002* (2013.01); *C07C 45/38* (2013.01); *C07C 51/00* (2013.01); *C07C 67/00* (2013.01); *C10G 3/42* (2013.01); *C10G 3/45* (2013.01); *C10G 3/49* (2013.01); *B01J 23/002* (2013.01); *B01J 25/00* (2013.01); *B01J 2229/42* (2013.01); *B01J 2523/00* (2013.01); *C01B 2203/0277* (2013.01); *C07C 2529/46* (2013.01); *C10G 2400/30* (2013.01); *Y02P 30/20* (2015.11)

(56) References Cited

U.S. PATENT DOCUMENTS

| | | |
|---|---|---|
| 3,894,103 A | 7/1975 | Chang |
| 3,894,104 A | 7/1975 | Chang |
| 3,894,105 A | 7/1975 | Chang |
| 3,894,106 A | 7/1975 | Chang |
| 3,907,915 A | 9/1975 | Chang |
| 3,998,898 A | 12/1976 | Chang |
| 4,039,600 A | 8/1977 | Chang |
| 4,076,761 A | 2/1978 | Chang |
| 4,220,803 A | 9/1980 | Marcinkowsky et al. |
| 4,308,411 A | 12/1981 | Frankiewicz |
| 4,359,587 A | 11/1982 | Abdurakhmanov et al. |
| 4,383,124 A | 5/1983 | de Graaf et al. |
| 4,663,492 A | 5/1987 | Chester et al. |
| 4,789,502 A | 12/1988 | Slaugh |
| 6,699,457 B2 | 3/2004 | Cortright et al. |
| 6,953,873 B2 | 10/2005 | Cortright et al. |
| 6,964,757 B2 | 11/2005 | Cortright et al. |
| 7,767,867 B2 | 8/2010 | Cortright |
| 7,977,517 B2 | 7/2011 | Cortright et al. |
| 8,017,818 B2 | 9/2011 | Cortright et al. |
| 8,053,615 B2 | 11/2011 | Cortright et al. |
| 8,231,857 B2 | 7/2012 | Cortright et al. |
| 8,350,108 B2 | 1/2013 | Cortright et al. |
| 8,395,002 B2 | 3/2013 | Babicki et al. |
| 8,492,600 B2 | 7/2013 | Marker et al. |
| 2010/0324314 A1* | 12/2010 | Imazeki .............. C07C 67/08 549/484 |

OTHER PUBLICATIONS

PCT International Search Report and Written Opinion, PCT/US2011/062341, dated Aug. 20, 2012.

Inaba, Megumu, et al. "Ethanol conversion to aromatic hydrocarbons over several zeolite catalysts." Reaction Kinetics and Catalysis Letters 88.1 (2006): 135-142.

Agency for Toxic Substances and Disease Registry, Gasoline Chemical Identity, Centers for Disease Control, p. 107-111, http://www.atsdr.cdc.gov/toxprofiles/tp72-c3.pdf.

Fuhse, Jürgen, and Friedhelm Bandermann. "Conversion of organic oxygen compounds and their mixtures on H-ZSM-5." Chemical engineering & technology 10.1 (1987): 323-329.

Sinnott, R.K., Coulson & Richardson's Chemical Engineering, Chemical Engineering Design, vol. 6, Fourth Edition, 2005, p. 50.

* cited by examiner

DEHYDROGENATION OF ALKANOLS TO INCREASE YIELD OF AROMATICS

CROSS-REFERENCE TO RELATED APPLICATIONS

This application is a continuation of U.S. application Ser. No. 13/900,400 filed on May 22, 2013, which is a continuation-in-part of U.S. application Ser. No. 13/304,052 filed on Nov. 23, 2011. Each of these applications is incorporated by reference herein in its entirety.

TECHNICAL FIELD

The present invention is directed to catalysts and methods for increasing aromatic yield in processes for converting alkanols to hydrocarbons.

BACKGROUND OF THE INVENTION

Aromatic hydrocarbons, notably benzene, toluene and ortho- and para-xylene (collectively, mixed xylenes), are important industrial commodities used, for example, to produce numerous chemicals, fibers, plastics, and polymers, including styrene, phenol, aniline, polyester, and nylon.

Mixtures of aromatic- and paraffinic hydrocarbons can be produced by converting alkanols in the presence of an oxygenate conversion catalyst, such as a zeolite catalyst. For example, methanol can be converted to gasoline range paraffins, aromatics, and olefins. Higher alcohols, such as ethanol, n-propanol, isopropanol, n-butanol, 2-butanol, isobutanol, tert-butyl alcohol, pentanol, and hexanol, can also be converted to hydrocarbons using this process.

When oxygenates are converted to hydrocarbons in the presence of a zeolite catalyst, the hydrogen-to-carbon effective ratio ($H:C_{eff}$ ratio) of the reactants affects the $H:C_{eff}$ ratio of the reaction products. The $H:C_{eff}$ ratio is calculated as follows:

$$H:C_{eff} = \frac{H - 2O}{C},$$

where H represents the number of hydrogen atoms, O represents the number of oxygen atoms, and C represents the number of carbon atoms. Water and molecular hydrogen (diatomic hydrogen, $H_2$) are excluded from the calculation. The $H:C_{eff}$ ratio applies both to individual components and to mixtures of components, but is not valid for components which contain atoms other than carbon, hydrogen, and oxygen. For mixtures, the C, H, and O are summed over all components exclusive of water and molecular hydrogen. The term "hydrogen" refers to any hydrogen atom while the term "molecular hydrogen" is limited to diatomic hydrogen, $H_2$. For illustration purposes, the $H:C_{eff}$ ratio of ethanol (and of all alkanols) is 2, as shown in Table 1 below.

TABLE 1

| $H:C_{eff}$ Ratio of Alcohols | |
|---|---|
| Alcohol (by number of carbon atoms) | $H:C_{eff}$ |
| C | 2 |
| $C_2$ | 2 |
| $C_3$ | 2 |

TABLE 1-continued

| $H:C_{eff}$ Ratio of Alcohols | |
|---|---|
| Alcohol (by number of carbon atoms) | $H:C_{eff}$ |
| $C_4$ | 2 |
| $C_5$ | 2 |
| $C_6$ | 2 |
| $C_7$ | 2 |
| $C_8$ | 2 |
| $C_9$ | 2 |
| ↓ | ↓ |
| $C_\infty$ | 2 |

Paraffins generally have a $H:C_{eff}$ ratio greater than 2, while alkyl mono-aromatic compounds generally have a $H:C_{eff}$ ratio between 1 and 2, as shown in Tables 2 and 3 below.

TABLE 2

| $H:C_{eff}$ Ratio of Paraffins | |
|---|---|
| Paraffins | $H:C_{eff}$ |
| $C_1$ | 4 |
| $C_2$ | 3 |
| $C_3$ | 2.67 |
| $C_4$ | 2.5 |
| $C_5$ | 2.4 |
| $C_6$ | 2.33 |
| $C_7$ | 2.29 |
| $C_8$ | 2.25 |
| $C_9$ | 2.22 |
| ↓ | ↓ |
| $C_\infty$ | 2 |

TABLE 3

| $H:C_{eff}$ Ratio of Alkyl Substituted Mono-Aromatics | |
|---|---|
| Aromatic | $H:C_{eff}$ |
| Benzene | 1.0 |
| Toluene | 1.14 |
| Xylene | 1.25 |
| $C_9$ | 1.33 |
| ↓ | ↓ |
| $C_\infty$ | 2 |

Other species of interest include carbon dioxide ($CO_2$) with a $H:C_{eff}$ ratio of −4, carbon monoxide (CO) with a $H:C_{eff}$ ratio of −2, and carbon (C) with a $H:C_{eff}$ ratio of 0. Carbonaceous residue, or coke, that may accumulate on catalyst or other surfaces exhibits a range of $H:C_{eff}$ ratios, depending on the amount of residual hydrogen and oxygen within the coke.

For the conversion of alkanols to hydrocarbons, many feeds of interest are essentially free of atoms other than C, H, and O, allowing from a practical standpoint the characterization of the feed to a reaction step using the $H:C_{eff}$ ratio and the products of a reaction step using the $H:C_{eff}$ ratio. For instance, alkanols can react across zeolite catalysts to form a mixture of hydrocarbons. Because of the high $H:C_{eff}$ ratio of alkanols, conversion of alkanols across zeolite catalysts generally yields a relatively high ratio of paraffins to aromatics—approximately three moles of paraffins are generated per mole of benzene or alkyl-substituted mono-aromatics. This is a desirable mixture for some applications, such as gasoline production. However, the low yield of aromatics limits the application of this process for the production of high value aromatic chemicals such as benzene, toluene, and xylenes (BTX).

Zhang et al. recently studied the impact of the H:$C_{\text{eff}}$ ratio on the conversion of biomass-derived feedstocks to coke, olefins and aromatics using a ZSM-5 catalyst (Zhang et al., *Catalytic conversion of biomass-derived feedstocks into olefins and aromatics with ZSM-5: the hydrogen to carbon effective ratio*, Energy Environ. Sci., 2011, 4, 2297). In this study, Zhang reported that biomass derived feedstocks having H:$C_{\text{eff}}$ ratios of between 0 and 0.3 produced high levels of coke, making it uneconomical to convert biomass derived feedstocks to aromatics and chemicals. Zhang also reported that the aromatic+olefin yield increases and the coke yield decreases with increasing H:$C_{\text{eff}}$ ratio of the feed. However, there is an inflection point at a H:$C_{\text{eff}}$ ratio of 1.2, where the aromatic+olefin yield does not increase as rapidly. The ratio of olefins to aromatics also increases with increasing H:$C_{\text{eff}}$ ratio, while CO and $CO_2$ yields go through a maximum with increasing H:$C_{\text{eff}}$ ratio. Specifically, Zhang reported that the aromatic and olefin yields increased from 12% and 15% to 24% and 56% with increasing H:$C_{\text{eff}}$ ratio, respectively, and that the olefin yield is higher than the aromatic yield for all feedstocks, with the gap increasing with an increase of the H:$C_{\text{eff}}$ ratio. Once again, this low yield of aromatics limits the application of the Zhang process for the production of high value aromatic chemicals such as benzene, toluene, and xylenes (BTX).

There remains a need for a method to increase the yield of aromatic hydrocarbons produced when converting alkanols to hydrocarbons.

SUMMARY OF THE INVENTION

The invention provides methods for converting alkanols to aromatic hydrocarbons. The method generally involves: (1) exposing an alkanol feedstock to a dehydrogenation catalyst at a dehydrogenation temperature between about 80° C. and 500° C. and a dehydrogenation pressure between about atmospheric pressure and 1000 psig to produce hydrogen and an oxygenate mixture having an H:$C_{\text{eff}}$ ratio of between about 1.0 and 1.8 and comprising two or more oxygenates selected from the group consisting of alcohols, carboxylic acids, esters and aldhehydes; and (2) exposing the oxygenate component to an oxygenate conversion catalyst at an oxygenate conversion temperature between about 250° C. and 550° C. and an oxygenate conversion pressure between about atmospheric pressure and 1000 psig, to produce aromatic hydrocarbons, wherein the carbon yield of aromatic hydrocarbons from the alkanol feedstock is greater than 40%.

One aspect of the invention is that the oxygenate mixture has a desired hydrogen to carbon effective ratio (H:$C_{\text{eff}}$ ratio). In one embodiment, the oxygenate mixture has a hydrogen to carbon effective ratio of less than 2.0, 1.9, 1.8, 1.7 or 1.6. In another embodiment, the oxygenate mixture has a hydrogen to carbon effective ratio of greater than 1.0, 1.1, 1.2, 1.3 1.4 or 1.5. In yet another embodiment, the oxygenate mixture has a hydrogen to carbon effective ratio between 1.2 and 1.8, or 1.2 and 1.6.

When the dehydrogenation and oxygenate conversion are complete, some of the carbon from the alkanol feedstock is contained within the aromatic hydrocarbons. In one embodiment, more than 45% of carbon in the alkanol feedstock is contained within the aromatic hydrocarbon product. In another embodiment, more than 50% of carbon in the alkanol feedstock is contained within the aromatic hydrocarbon product.

Another aspect of the invention is the composition of the alkanol feedstock. In one embodiment the alkanol feedstock is derived from material of recent biological origin such that the age of the compounds, or fractions containing the compounds, is less than 100 years old, preferably less than 40 years old, and more preferably less than 20 years old, as calculated from the carbon 14 concentration of the feedstock. In other embodiments, the alkanol feedstock comprises a primary alcohol, ethanol, n-butanol, 2-butanol, isobutanol, n-pentanol, n-hexanol, ethylene glycol, propylene glycol, glycerol, erythritol, threitol and sugar alcohols. In other embodiments, the alkanol feedstock is derived from a fermentation, Fischer-Tropsch, pyrolysis, aqueous phase reforming or other catalytic conversion process.

When the alkanol feedstock is exposed to a dehydrogenation catalyst at a dehydrogenation temperature and pressure, hydrogen and an oxygenate mixture is produced. In one embodiment, the oxygenate mixture comprises a carboxylic acid, an aldehyde, an ester and an alcohol, with the concentration of the carboxylic acid in the oxygenate mixture less than 20% of the carbon in the oxygenate mixture. In one embodiment, the oxygenate mixture comprises a carboxylic acid, an aldehyde, and an ester, with the concentration of the carboxylic acid in the oxygenate mixture less than 30% of the carbon in the oxygenate mixture. In other embodiments, the oxygenate mixture comprises an ester, or the oxygenate mixture comprises an aldehyde.

The dehydrogenation catalyst is a catalyst capable of dehydrogenating alkanols to form the oxygenate mixture. In one embodiment, the dehydrogenation catalyst comprises a metal selected from the group consisting of Cu, Ru, Ag, CuCr, CuZn, Co, alloys thereof, and combinations thereof. The dehydrogenation catalyst may further comprise a support. The support may comprise a material selected from the group consisting of alumina, silica, silica-alumina, titania, carbon, zirconia, and mixtures thereof. In one embodiment, the dehydrogenation catalyst comprises Cu on a silica support. In another embodiment, the dehydrogenation catalyst comprises Raney copper or copper zinc aluminate.

The dehydrogenation reaction is conducted at a temperature and pressure where the thermodynamics are favorable. In one embodiment, the dehydrogenation temperature is between about 80° C. and 500° C., and the dehydrogenation pressure ranges from atmospheric pressure to about 1000 psig. In another embodiment, the dehydrogenation temperature is between about 150° C. and 400° C. In yet another embodiment, the dehydrogenation pressure is between 75 psig and about 1000 psig. In still yet another embodiment, the dehydrogenation pressure is between 100 psig and about 500 psig.

The aromatic hydrocarbons are produced by catalytically reacting the oxygenate mixture in the presence of an oxygenate conversion catalyst at a oxygenate conversion temperature and an oxygenate conversion pressure. In one embodiment, the oxygenate conversion catalyst comprises a zeolite. In another embodiment, the oxygenate conversion catalyst is ZSM-5. In yet another embodiment, the oxygenate conversion catalyst is a nickel modified ZSM-5 catalyst. The oxygenate conversion catalyst may be modified by a material selected from the group consisting of phosphorous, gallium, zinc, nickel, tungsten, and mixtures thereof. The oxygenate conversion catalyst may also contain a binder selected from the group consisting of alumina, silica, silica-alumina, titania, zirconia, aluminum phosphate, and mixtures thereof.

The oxygenate conversion reaction is conducted at a temperature and pressure where the thermodynamics are favorable. In one embodiment, the oxygenate conversion temperature is between about 250° C. and 550° C., and the oxygenate conversion pressure is less than 400 psig.

Another aspect of the invention is a method of producing hydrocarbons by catalytically reacting an alkanol feedstock with a multi-functional dehydrogenation/oxygenate conversion catalyst at a temperature and pressure suitable to produce hydrocarbons.

Another aspect of the invention is a method of converting ethanol to aromatic hydrocarbons, the method comprising the steps or acts of: (1) exposing an ethanol feedstock to a dehydrogenation catalyst at a dehydrogenation temperature of between about 80° C. and 500° C. and a dehydrogenation pressure of between about 75 psig and 1000 psig to produce an oxygenate mixture comprising ethanol, acetaldehyde, acetic acid, and ethyl acetate, wherein the oxygenate mixture has an $H:C_{\mathit{eff}}$ ratio of between about 1.0 and 1.8 and an acetic acid concentration of less than 20% of the carbon in the oxygenate mixture, and (2) exposing the oxygenate mixture to an oxygenate conversion catalyst at an oxygenate conversion temperature between about 250° C. and 550° and an oxygenate conversion pressure between about atmospheric pressure and 500 psig to produce aromatic hydrocarbons, wherein the carbon yield of aromatic hydrocarbons from the ethanol feedstock is greater than 40%.

DETAILED DESCRIPTION OF THE INVENTION

Figure 1:
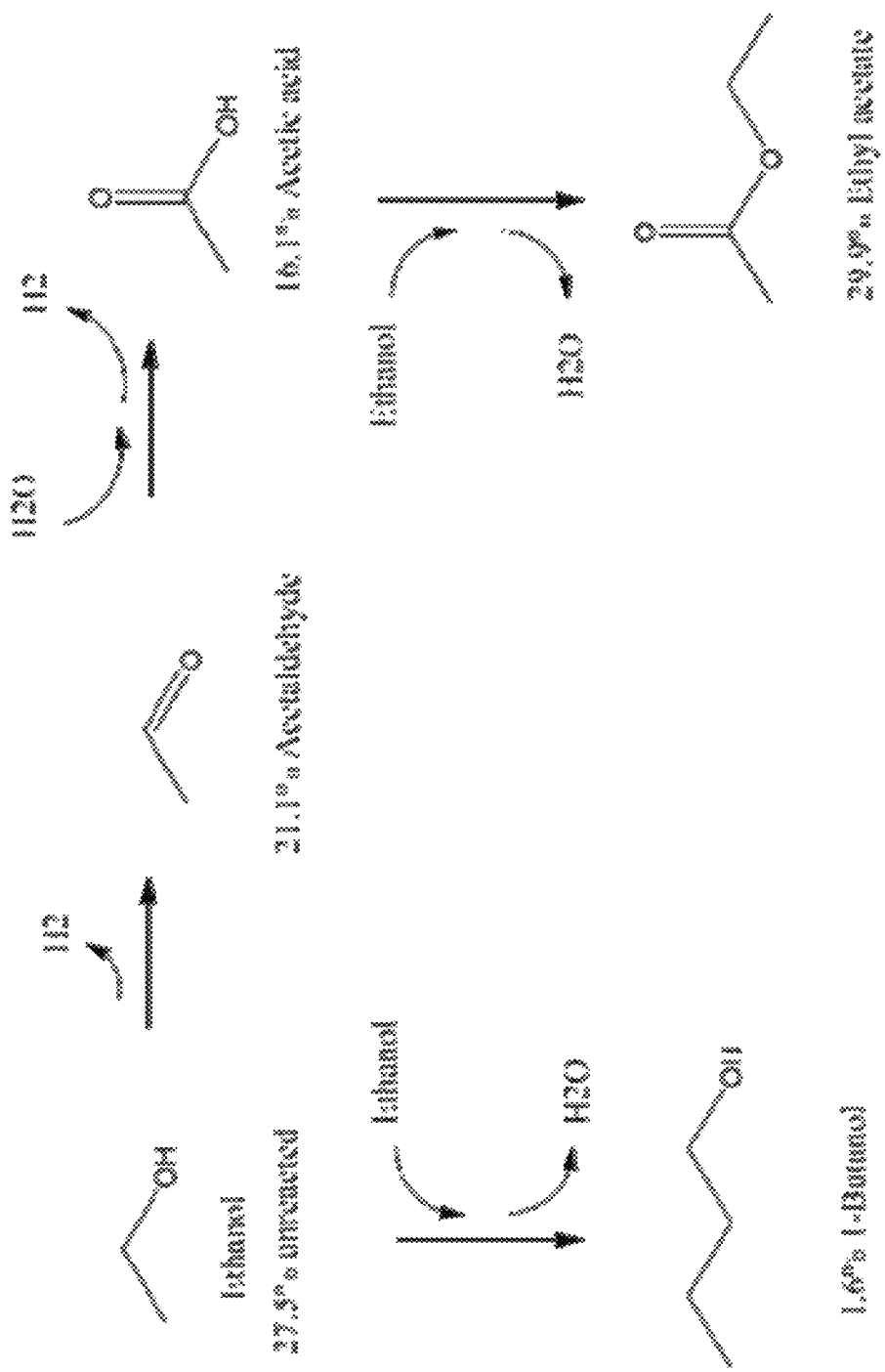
FIG. 1 is an illustration of the chemistry involved in one aspect of the present invention using ethanol as the feedstock.

The present invention relates to methods, reactor systems, and catalysts for increasing the yield of aromatic hydrocarbons produced while converting alkanols to hydrocarbons. The invention includes methods of using catalysts to increase the yield of benzene, toluene, and mixed xylenes in the hydrocarbon product.

As used herein, the term "alkanols" refers to, without limitation, aliphatic alcohols with the general formula $C_nH_{2n+2}O_1$. Alkanols suitable for use in feedstocks in accord with the invention include $C_1$ to $C_6$ alkanols, which can be primary, secondary or polyhydric alcohols, such as one or more of methanol, ethanol, n-propanol, iso-propanol, n-butanol, 2-butanol, isobutanol, n-pentanol, n-hexanol, ethylene glycol, propylene glycol, glycerol, erythritol, threitol and sugar alcohols. Tertiary alcohols are less preferred as sole components of an alkanol feedstock, but can be used when combined with more suitable primary or secondary alcohols.

The alkanols may originate from any source, but are preferably derived from biomass. As used herein, the term "biomass" refers to, without limitation, organic materials produced by plants (such as leaves, roots, seeds and stalks), and microbial and animal metabolic wastes. Common sources of biomass include: (1) agricultural wastes, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; and (4) energy crops, such as poplars, willows, switch grass, alfalfa, prairie bluestream, corn, soybean, and the like. The term also refers to the primary building blocks of the above, namely, saccharides, lignin, cellulosics, hemicellulose and starches, among others.

Alkanols from biomass may be produced by any known method. Such methods include fermentation technologies using enzymes or microorganisms, Fischer-Tropsch reactions to produce $C_{2-10}$ alpha alcohols, and pyrolysis technologies to produce alcohols from oil, among others. In one embodiment, the alkanols are produced using catalytic reforming technologies, such as the BioForming® technology developed by Virent, Inc. (Madison, Wis.), and described in U.S. Pat. No. 7,767,867 (Cortright), U.S. Pat. No. 7,898,664 (Cortright), U.S. Pat. No. 8,053,615 (Cortright et al.), U.S. Pat. No. 8,017,818 (Cortright et al.), and U.S. Pat. No. 7,977,517 (Cortright et al.), all of which are incorporated herein by reference. The alkanols may also be derived from natural gas using Fischer-Tropsch type reactions.

Surprisingly, the inventors increased the yields of aromatic hydrocarbons by partially dehydrogenating alkanol feedstocks using a dehydrogenation catalyst in the below described reaction environment. Without being bound to any particular theory, the inventors believe that hydrogen atoms, made available through the conversion of relatively hydrogen-rich alkanols to aromatics, can be transferred to unsaturated components by the catalyst. If the hydrogen is transferred to an olefin, a paraffin is generated. Because olefins are precursors to aromatics, the conversion of an olefin to a paraffin reduces the available pool of material able to be converted to aromatics. If the hydrogen is transferred to a ketone or aldehyde, an alkanol is formed. In this manner, the carbonyl group of the ketone or aldehyde acts as a hydrogen sink, removing reactive hydrogen and preventing the conversion of olefins to paraffins, thereby reducing the amount of paraffins and increasing the overall aromatics yield. The resulting alkanol is also productive as it serves as additional feedstock for the hydrocarbon forming reactions.

As used herein, oxygenates capable of reacting with hydrogen in this manner are termed "hydrogen acceptors". It is believed that carbonyls, carboxylic acids, esters, cyclic ethers, diols, polyols, furans and other oxygenates characterized by having a $H:C_{\mathit{eff}}$ ratio of <2 are capable of being hydrogen acceptors, either directly or following other reactions (such as dehydration), which have converted the components to hydrogen acceptors. The net impact of transferring hydrogen to unsaturated oxygenates is to produce fewer paraffins and increase the aromatic hydrocarbon yield.

The alkanol feedstock may include any one or more alkanols or mixtures thereof. In one embodiment, the alkanol feedstock includes ethanol. The oxygenates produced from ethanol generally include acetaldehyde, acetic acid, and ethyl acetate. During the claimed reaction, primary alkanols produce the equivalent products corresponding to the carbon number of the starting alkanol. Secondary alcohols are unable to proceed to acids or esters and will produce primarily ketones, unless used in a mixture with other alkanols. The specific products depend on various factors, including the composition of the alkanol feedstock, reaction temperature, reaction pressure, alkanol concentration, the reactivity of the catalyst, and the flow rate of the alkanol feedstock as it affects the space velocity (the mass/volume of reactant per unit of catalyst per unit of time).

Ethers may also be produced from alkanols. For instance, the conversion of methanol to dimethyl ether can be used to reduce the exotherm of oxygenate conversion. Dialkyl ethers may also be present in the feed to the oxygenate conversion catalyst as a product of the dehydrogenation catalyst or as a separately fed component. Dialkyl ethers, such as diethylether, dimethylether, etc., have a $H:C_{eff}$ ratio of 2.0 and, as such, impact the aromatic to paraffin ratio of the product the same as an alkanol.

As indicated above, the $H:C_{eff}$ ratio of the reactants impact the $H:C_{eff}$ ratio of the reaction products. When the hydrogen acceptors are passed as reactants over an oxygenate conversion catalyst, an improved aromatic hydrocarbon yield is realized, relative to the yield realized when the reactants are alkanols. The $H:C_{eff}$ ratio of the aldehydes that may be formed by dehydrogenation of primary alkanols is between zero and 2 as shown in Table 4 below.

TABLE 4

$H:C_{eff}$ Ratio of Aldehydes and Ketones

| Aldehydes or Ketone carbon number | $H:C_{eff}$ |
|---|---|
| $C_1$ | 0 |
| $C_2$ | 1.0 |
| $C_3$ | 1.33 |
| $C_4$ | 1.5 |
| $C_5$ | 1.6 |
| $C_6$ | 1.67 |
| $C_7$ | 1.71 |
| $C_8$ | 1.75 |
| $C_9$ | 1.78 |
| ↓ | ↓ |
| $C_\infty$ | 2 |

In accordance with the invention, the process for converting alkanols to hydrocarbons can be a two-step process (in which the dehydrogenation catalyst and the oxygenate conversion catalyst are separate catalysts) or a one-step process (in which the dehydrogenation catalyst and the oxygenate conversion catalyst are combined to provide a single multifunctional catalyst). When separate catalysts are provided, they may be present in separate vessels, in separate beds within a single vessel, in alternating layers in a single bed of catalyst, or physically mixed within the same bed.

The general two-step process is as follows. An alkanol feedstock is first passed into contact with a dehydrogenation catalyst in a reactor at a dehydrogenation temperature and a dehydrogenation pressure, thereby releasing molecular hydrogen and producing an oxygenate mixture. The alkanol feedstock may be an essentially pure alkanol stream or, alternatively, the alkanol feedstock may be mixed with water to create an aqueous solution wherein the alkanol concentration is greater than 20 wt %, or greater than 30 wt %, or greater than 40 wt %, or greater than 50 wt %, or greater than 60 wt %, or greater than 72 wt %, or greater than 80 wt %, or greater than 90 wt %, or greater than 95 wt %. Alternatively, the alkanol feedstock may include a mixture of other alcohols or oxygenates to provide a mixed alkanol feedstock stream. FIG. 1 illustrates the components of one oxygenate mixture in which ethanol is used as the alkanol feedstock.

The dehydrogenation catalyst includes one or more materials of metal and/or basic functionality capable of catalyzing the conversion of hydroxyl elements to carbonyls. Suitable metallic components include, without limitation, Cu, Ru, Ag, CuCr, CuZn, Co, Sn, Mo, and combinations thereof. Suitable base-catalyzed dehydrogenation catalysts include Li, Na, K, Cs, Mg, Ca, Ba, Zn, Ce, La, Y, Zr, hydrotalcite, base-treated aluminosilicate zeolite. The base catalyst may also include an oxide of Ti, Zr, V, Mo, Cr, Mn, Al, Ga, Co, Ni, Si, Cu, Zn, Sn, Mg, P, Fe, and combinations thereof. Preferred Group IA materials include Li, Na, K, and Cs. Preferred Group IIA materials include Mg, Ca, and Ba. A preferred Group IIB material is Zn. Preferred Group IIIB materials include Y and La. Basic resins include resins that exhibit basic functionality, such as Amberlyst A26 and Amberlyst A21. The base catalyst may be self-supporting or adhered to any one of the supports further described below, including supports containing carbon, silica, alumina, zirconia, titania, vanadia, ceria, alloys and mixtures thereof.

The base catalyst may also include zeolites and other microporous supports that contain Group IA compounds, such as Li, Na, K, and Cs. Preferably, the Group IA material is present in an amount greater than that required to neutralize the acidic nature of the support. These materials may be used in any combination, and also in combination with alumina or silica. A metal function may also be provided by the addition of group VIIIB metals, or Cu, Ga, In, Zn, Cr, or Sn.

The dehydrogenation catalyst is either self-supporting or, preferably, includes a supporting material. The support for the metallic component may contain any one or more of alumina, silica, silica-alumina, titania, carbon, zirconia, and mixtures thereof. Copper on a silica support, Raney copper, and copper-zinc-aluminate are particularly preferred dehydrogenation catalysts. For the copper catalyst on a silica support, the copper content may generally range from 0.05% to 40%, preferably from 0.1% to 20%, and most preferably from 0.2% to 10%.

In some embodiments, the dehydrogenation temperature is between about 80° C. and 500° C., preferably between about 100° C. and 450° C., and most preferably between about 150° C. and 400° C. In one embodiment, the dehydrogenation temperature is greater than 80° C., or is greater than 100° C., or is greater than 150° C., and less than 500° C., or less than 450° C., or less than 400° C.

The dehydrogenation pressure ranges from atmospheric pressure up to about 1000 psig, or from about atmospheric pressure to about 700 psig, or from about 75 psig to about 1000 psig, or from about 75 psig to about 700 psig, or from about 100 psig to about 500 psig. In one embodiment, the dehydrogenation pressure is greater than atmospheric pressure, or greater than 75 psig, or greater than 100 psig, and less than 1000 psig, or less than 700 psig, or less than 500 psig.

The extent to which the alkanol feed stock is dehydrogenated can be measured by the amount of molecular hydrogen released during dehydrogenation and may range from 0.05 to 2.0 moles of molecular hydrogen released per mole of alkanol feed. Values greater than 1 mole of molecular hydrogen released per mole of feed are possible when carbonyls are further converted to acids, with an associated consumption of water and release of molecular hydrogen. In general, the reaction should be conducted under conditions where the residence time of the alkanol feedstock over the catalyst is appropriate to generate the desired dehydrogenation products. For example, the residence time may be established at a weight hourly space velocity (WHSV) of between 0.01 and 30, or between 0.05 and 10, or between 0.1 and 5, or between 1.0 and 4.

Desirable levels of dehydrogenation depend on the composition of the alkanol feedstock. To produce a shift in the aromatic-to-paraffin ratio during the oxygenate conversion, longer chain alcohols must be dehydrogenated to a greater extent than short chain alcohols. For a methanol feedstock, less than 50% dehydrogenation is desirable (0.5 moles of molecular hydrogen released per mole of total feedstock to the system), and less than 37% is preferred to prevent an excessive coking rate. For an ethanol feedstock, less than 85% dehydrogenation is desirable (0.85 moles of molecular hydrogen released per mole of total feedstock to the system), and less than 75% is preferred. For mixed alkanol feedstocks, the overall extent of dehydrogenation should be such that the overall H:$C_{\mathit{eff}}$ ratio is less than 2.0, 1.9, 1.8, 1.7 or 1.6, and greater than 1.0, 1.1, 1.2, 1.3, 1.4 or 1.5. For example, the overall extent of dehydrogenation should be such that the carbon effective ratio is between 1.0 and 1.8, or between 1.2 and 1.8, or between 1.2 and 1.6. For alkanols containing three or more carbons, any level up to complete dehydrogenation may be desirable. Dehydrogenation extent may be controlled by varying the catalyst, the operating conditions, and the feedstock composition. Higher temperatures generally lead to greater levels of dehydrogenation.

Hydrogen may be added to the reaction to limit the extent of dehydrogenation and to prevent deactivation of the dehydrogenation catalyst. When hydrogen is provided to the dehydrogenation reaction, it may be from an external hydrogen supply or recycled hydrogen from the dehydrogenation process. When used, suitable ratios of hydrogen to alcohol in the feed include about 0.1, 0.2, 0.3, 0.4, 0.5, 0.6, 0.7, 0.8, 0.9, 1.0, and 2.0 moles of hydrogen to moles alcohol in the feed. For ethanol, any aqueous solution that contains greater than 72 wt % ethanol has a mole ratio of water to ethanol which is less than one.

Water may also be present or added to the feed. The presence of water increases the potential amount of hydrogen released from the dehydrogenation reaction by enabling a portion of the alkanol feed to be converted to a carboxylic acid. The generation of carboxylic acids consumes water while releasing additional hydrogen. Therefore, in order to generate carboxylic acids, water must be present. However, it is not the intent of the current invention to generate high levels of carboxylic acids. Accordingly, substoichiometric amounts of water, less than one mole of water per mole of alkanol feed, in the alkanol feedstock stream is preferred. When generated, carboxylic acids preferably make up less than about 30% of the carbon in the oxygenate mixture, or less than 20% of the carbon in the oxygenate mixture, or less than 15% of the carbon in the oxygenate mixture, or less than 10% of the carbon in the oxygenate mixture, or less than 5% of the carbon in the oxygenate mixture.

Other components, such as additional oxygenates and hydrogen, may be added to the oxygenate mixture prior to oxygenate conversion. If additional components are added, it may be preferable to dehydrogenate smaller chain alcohols such as methanol and ethanol to a greater extent so that the overall H:$C_{\mathit{eff}}$ ratio is between 1.0 and 1.8, and preferably between 1.2 and 1.7.

The oxygenate mixture, including unreacted alcohols and the hydrogen acceptors, are then passed in whole or in part into contact with an oxygenate conversion catalyst in a reactor under conditions of temperature and pressure effective to convert a portion of the dehydrogenation products to aromatic hydrocarbons. The oxygenate conversion catalyst has one or more acidic materials capable of catalyzing the conversion of dehydrogenation products to the desired aromatic hydrocarbons. The conversion catalyst may include, without limitation, aluminosilicates (zeolites), silica-alumina phosphates (SAPO), aluminum phosphates (ALPO), amorphous silica alumina, zirconia, sulfated zirconia, tungstated zirconia, titania, acidic alumina, phosphated alumina, phosphated silica, sulfated carbons, phosphated carbons, heteropolyacids, and combinations thereof. In one embodiment, the catalyst may also include a modifier, such as Ce, Y, Sc, La, P, B, Bi, Li, Na, K, Rb, Cs, Mg, Ca, Sr, Ba, and combinations thereof. The catalyst may also be modified by the addition of a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide metal functionality, and/or oxides of Ti, Zr, V, Nb, Ta, Mo, Cr, W, Mn, Re, Al, Ga, In, Fe, Co, Ir, Ni, Si, Cu, Zn, Sn, Cd, P, and combinations thereof. The conversion catalyst may be self-supporting or adhered to any one of the supports further described below, including supports containing carbon, silica, alumina, zirconia, titania, vanadia, ceria, heteropolyacids, alloys and mixtures thereof.

Ga, In, Zn, Fe, Mo, Ag, Au, Ni, P, Sc, Y, Ta, and lanthanides may also be exchanged onto zeolites to provide a zeolite catalyst. The term "zeolite" as used herein refers not only to microporous crystalline aluminosilicate but also for microporous crystalline metal-containing aluminosilicate structures, such as galloaluminosilicates and gallosilicates. Metal functionality may be provided by metals such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. Nos. 3,702,886; Re. 29,948 (highly siliceous ZSM-5); U.S. Pat. No. 4,100,262 and U.S. Pat. No. 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. No. 5,019,663 and U.S. Pat. No. 7,022,888, also incorporated herein by reference.

As described in U.S. Pat. No. 7,022,888, the acid catalyst may be a bifunctional pentasil zeolite catalyst including at least one metallic element from the group of Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, or a modifier from the group of Ga, In, Zn, Fe, Mo, Au, Ag, Y, Sc, Ni, P, Ta, lanthanides, and combinations thereof. The zeolite may be used with reactant streams containing an oxygenated hydrocarbon at a temperature of below 600° C. The zeolite may have ZSM-5, ZSM-8 or ZSM-11 type crystal structure consisting of a large number of 5-membered oxygen-rings, i.e., pentasil rings. The zeolite with ZSM-5 type structure is a particularly preferred catalyst. In one embodiment, the oxygenate conversion catalyst is a nickel modified ZSM-5 catalyst.

The catalyst may optionally contain any binder such as alumina, silica or clay material. The catalyst can be used in the form of pellets, extrudates and particles of different shapes and sizes. In one aspect, the oxygenate conversion catalysts are ZSM-5 and beta zeolite.

In general, the oxygenate conversion temperature is between about 250° C. and 550° C., preferably between about 300° C. and 500° C., and most preferably between about 320° C. and 480° C. The oxygenate conversion pressure ranges from below atmospheric pressure up to about 1000 psig, or from about atmospheric pressure to about 700 psig, or from about 10 psig to about 500 psig, or less than 400 psig. In one embodiment, the oxygenate conversion pressure is greater than atmospheric pressure, or greater than 10 psig, or greater than 100 psig, and less than 1000 psig, or less than 700 psig, or less than 500 psig, or less than 400 psig. In general, the reaction should be conducted under conditions where the residence time of the dehydrogenation products over the oxygenate conversion catalyst is appropriate to generate the desired hydrocarbons. For example, the residence time may be established at a weight hourly space velocity (WHSV) of between 0.01 and 30, or between 0.05 and 10, or between 0.1 and 5, or between 1.0 and 4.

Figure 2:
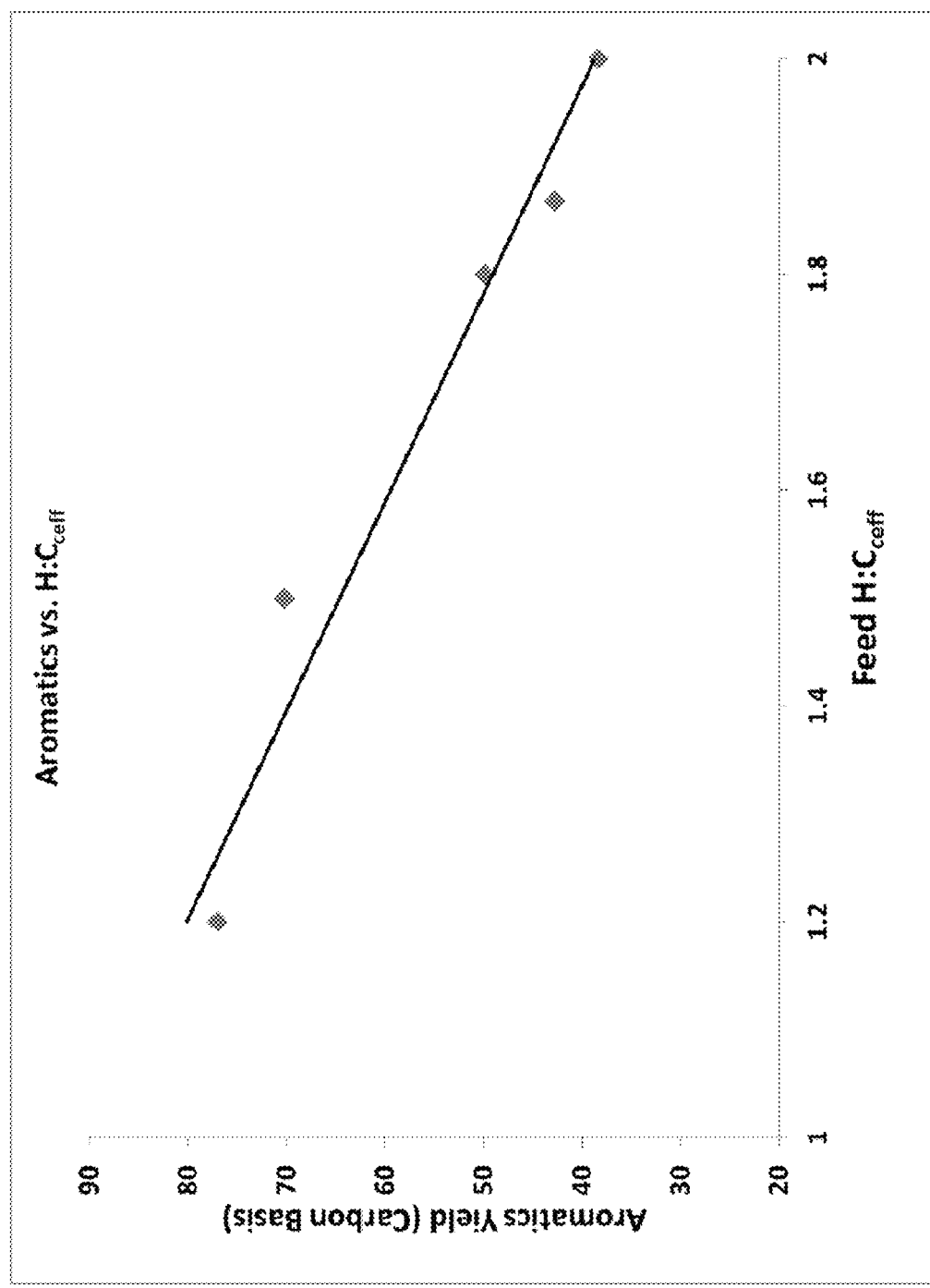
FIG. 2 is a chart illustrating increased aromatic yield in the claimed process versus traditional methods of converting alcohols to hydrocarbons as a function of the hydrogen-to-carbon effective ratio.
Figure 3:
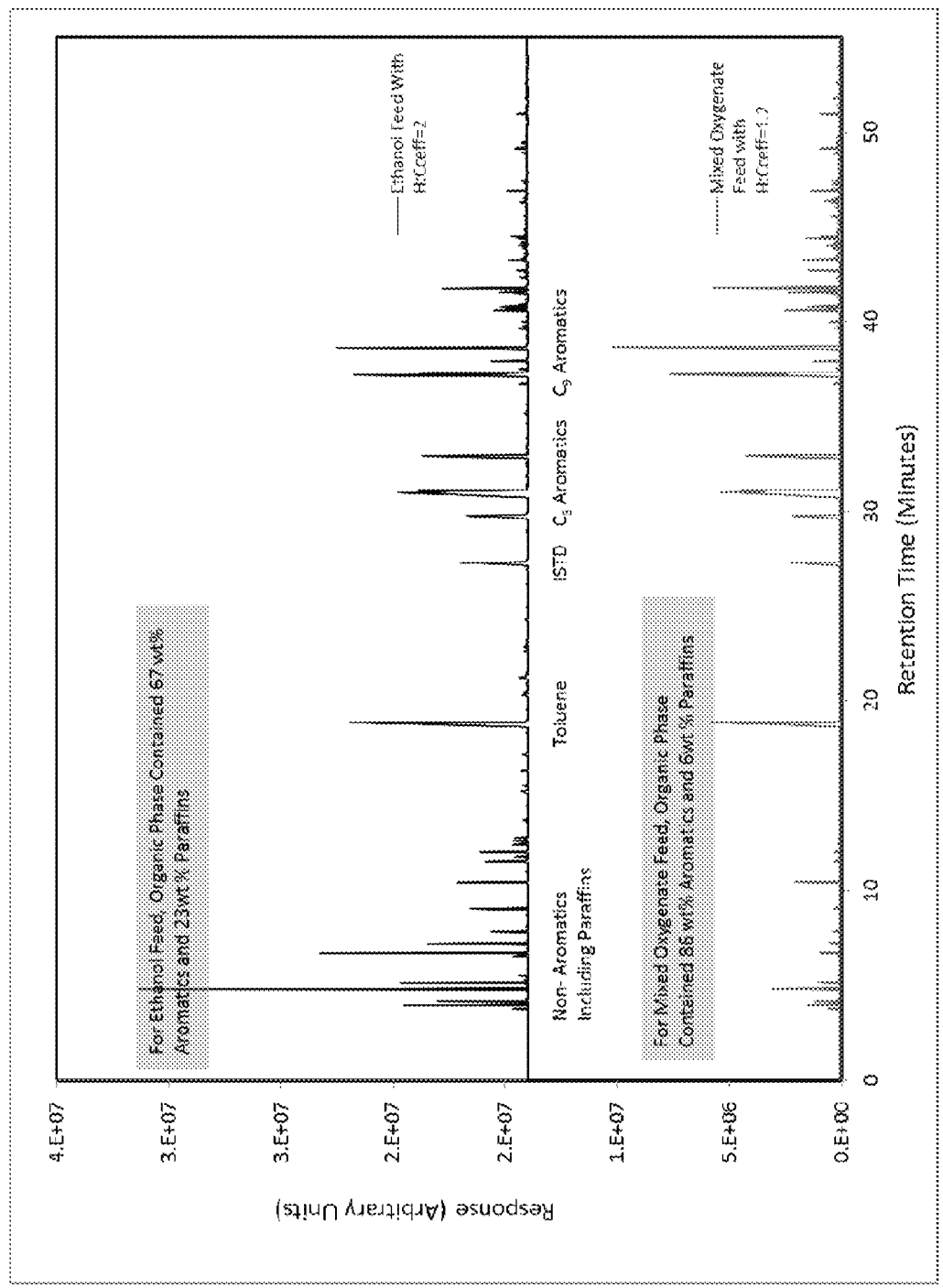
FIG. 3 is chart illustrating the shift in aromatic carbon yields associated with a decreased hydrogen-to-carbon effective ratio.

Excluding molecular hydrogen ($H_2$), the overall $H:C_{eff}$ ratio of the dehydrogenation products is generally less than 2, resulting in an increased yield of aromatics, and an improvement over traditional methods of converting alcohols to hydrocarbons. When the dehydrogenation and oxygenate conversion are complete, more than 40%, or 45%, or 50%, or 60%, or 70%, or 75%, of the carbon in the alkanol feedstock is contained within the aromatic hydrocarbon product. FIG. 2 shows the improved aromatic yield achieved by reducing the $H:C_{eff}$ ratio below 2. FIG. 3 shows the increase in liquid product aromatic content achieved by reducing the $H:C_{eff}$ ratio below 2. Additional oxygenated feed components may also be introduced into the second reactor.

Figure 4:
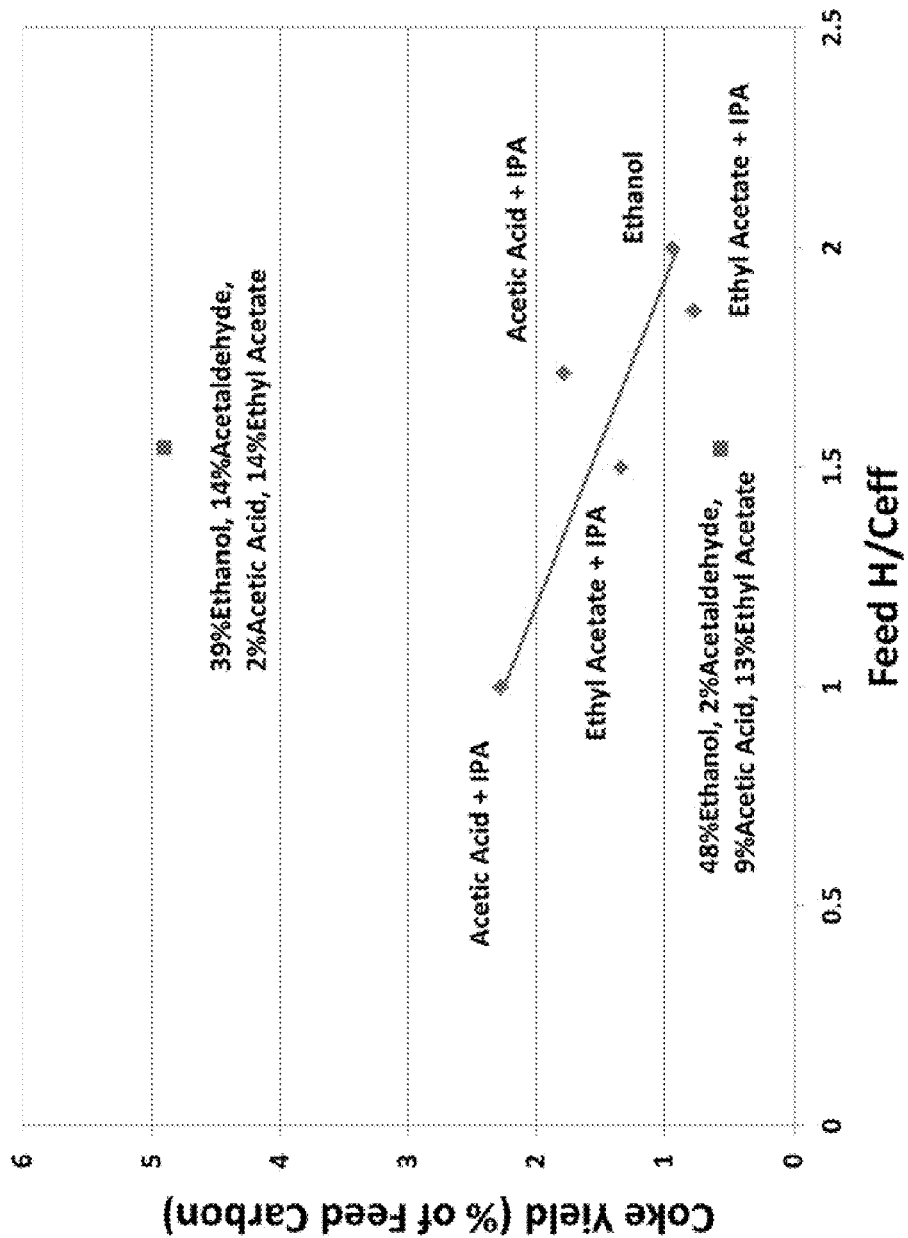
FIG. 4 is a chart illustrating typical coke yields obtained from the process for conversion of model compounds and dehydrogenation products across a ZSM-5 catalyst.

An important aspect of the invention is that the fraction of the feed carbon that forms coke on the condensation catalysts is limited. It is well known that many strategies for converting biomass into hydrocarbons suffer from high yields of carbon as coke (see Zhang et al. referenced above). This not only represents a loss of potential product yield, but also causes deactivation of the oxygenate conversion catalyst and requires the coke to be removed through oxidative regeneration or other regeneration approaches. Surprisingly, it was found that the coke yield could be controlled through the specific mix of the oxygenate mixture directed to the oxygenate conversion system. For example, FIG. 4 shows the coke yields resulting from the conversion of two different mixtures across a ZSM-5 condensation catalyst. At a similar $H:C_{eff}$, the yield of coke ranged from less than 1% of the carbon to greater than 4% of the carbon. This is in contrast to Zhang et al. where the primary determinant of coke yield was found to be the $H:C_{eff}$. Desirable coke yields from the process are less than 8%, or less than 7%, or less than 6%, or less than 5%, or less than 4%, or less than 3%, or less than 2%, or less than 1%, of the carbon in the feed.

There is generally some conversion of feedstock carbon to carbon dioxide and carbon monoxide (COx) across the oxygenate conversion catalyst, which results in a loss of potential product yield. Therefore, to obtain high yields of hydrocarbon product in general, and aromatics specifically, (COx) yield should be minimized. Suitable COx yields are less than 8%, or less than 7%, or less than 6%, or less than 5%, or less than 4%, or less than 3%, or less than 2%, or less than 1%, of the carbon in the feed.

The present invention may also be practiced as a one-step process in which the dehydrogenation catalyst and the oxygenate conversion catalyst is a multi-functional catalyst. In this approach, alkanols are converted to hydrocarbons employing a multi-functional catalyst having one or more materials capable of catalyzing both the dehydrogenation and oxygenate conversion reactions. The multi-functional catalyst may include any of the elements suitable for separate dehydrogenation and oxygenate conversion catalysts discussed above. One particularly useful catalyst is copper loaded onto silica-bound ZSM-5. In this single-step embodiment, the dehydrogenation reaction and the oxygenate conversion reactions occur in the same reaction vessel under conditions of temperature and pressure as described above and which are suitable for both the dehydrogenation and oxygenate conversion reactions to proceed.

In some embodiments, the products of the dehydrogenation step are separated to provide one or more streams which are directed to the conversion reactor and one or more streams which are not directly fed into the conversion reactor. The streams which are not directly fed into the conversion reactor may be removed from the system or recycled to the dehydrogenation reactor for further conversion. Means of separation include, without limitation, separation based on volatility differences between components, extraction, membranes, and ion exchange. In one preferred embodiment, the products of the dehydrogenation step are cooled and a portion of the molecular hydrogen produced in the reaction step is removed as a gas phase product prior to sending the remaining components to the conversion reactor. In another preferred embodiment, the dehydrogenation product is separated by distillation to provide an aldehyde enriched stream which is recycled to the dehydrogenation reactor to effect conversion of the aldehydes to acids and esters. In yet another preferred embodiment, Alkanols are separated from the product stream and recycled to the dehydrogenation reactor to increase the overall alkanol conversion.

In other embodiments, oxygenates other than alkanols may be used in addition to and as a supplement to the alkanol feedstock.

The following examples are to be considered illustrative of various aspects of the invention and should not be construed to limit the scope of the invention, which are defined by the appended claims.

EXAMPLES

Preparing Ethanol Dehydrogenation Catalysts

Example 1

Copper modified monoclinic zirconia was prepared by adding an aqueous solution of copper nitrate to monoclinic zirconia (Saint-Gobain Norpro, Ohio) using an incipient wetness impregnation technique to achieve a target copper loading of 1, 2 and 5 wt %. The catalyst was dried overnight under vacuum at 110° C. and calcined at 400° C. under flowing air for 6 hours.

Example 2

Copper nitrate (Acros, Geel, Belgium) was added to a gamma alumina support (Norpro Saint Gobain, Paris, France) using an incipient wetness impregnation technique to achieve a target Cu loading of 5 wt %. The catalyst was dried in an oven with an air purge at 120° C. and then calcined in the same oven with a temperature ramp of 2° C./min to 550° C. and held for 7 hours.

Example 3

Copper modified calcium doped gamma alumina catalyst was prepared by adding an aqueous solution of copper nitrate to calcium doped gamma alumina (Saint-Gobain Norpro, Ohio) using an incipient wetness impregnation technique to achieve a target copper loading of 2 wt %. The catalyst was dried overnight under vacuum at 110° C. and calcined at 400° C. under flowing air for 6 hours.

Example 4

Copper nitrate (Acros, Geel, Belgium) was added to a silica support (Davisil, grade 635, Sigma Aldrich, St Louis, Mo.) using an incipient wetness impregnation technique to achieve a target Cu loading of 5 wt %. The catalyst was dried in an oven with an air purge at 120° C. and then calcined in the same oven with a temperature ramp of 2° C./min to 550° C. and held for 7 hours.

Example 5

Raney copper (W. R. Grace) was directly used in the ethanol dehydrogenation testing after water washing and $H_2$ co-feed over the catalyst overnight.

Example 6

Copper-zinc-aluminate (Sud-Chemie, ShiftMax® 230) was sized to 18×30 mesh and used directly in ethanol dehydrogenation testing.

Ethanol Dehydrogenation

Example 7

The catalyst systems referenced in Examples 1-6 were investigated for dehydrogenation of ethanol. The studies were conducted in a 8.5 mm internal diameter size stainless steel tube reactor. 22 grams of catalyst were loaded into the reactor. In all cases, the catalyst was reduced at 350° C. under flowing hydrogen prior to use. A feedstock consisting of 95% ethanol in water was then passed over the catalyst under the conditions shown in Table 5.

The gas, organic (when present) and aqueous phases were collected and analyzed to determine product yields. Table 5 shows the reaction products as a function of operating conditions for the catalysts described in Examples 1 to 6. The overall extent of dehydrogenation can be gauged by the hydrogen yield, ranging from 0.18 to 0.84 moles of hydrogen produced per mole of ethanol fed.

Several reaction pathways are evident from the product profiles, due to functionality inherent in both the copper metal function and the supports. These reaction products were mixtures of oxygenates suitable for further processing into hydrocarbons. Importantly, the $H:C_{eff}$ ratio of the oxygenate mixtures were lower than that of the feed alkanol in all cases.

TABLE 5

Ethanol Dehydrogenation over Catalysts in Examples 1-6

| Catalyst | | 1% Cu/ mZrO2 | 2% Cu/ mZrO2 | 5% Cu/ mZrO2 | 5% Cu/ mZrO2 | 5% Cu/ γ-Al2O3 | 2% Cu/ Ca-γ-Al2O3 | 5% Cu/ SiO2 | Raney Cu | Shift Max 230 |
|---|---|---|---|---|---|---|---|---|---|---|
| WHSV | $wt_{feed}/(wt_{catalyst} hr)$ | 1.5 | 0.75 | 1.5 | 1.5 | 0.75 | 0.75 | 0.75 | 0.77 | 0.77 |
| Diluent Nitrogen | $molN_2/mol_{feed}$ | 0.11 | 0.22 | 0.11 | 0.11 | 0.11 | 0.22 | 0.11 | 0.11 | 0.11 |
| Temperature | ° C. | 350 | 350 | 300 | 350 | 300 | 350 | 350 | 325 | 300 |
| Pressure | Psig | 100 | 100 | 100 | 100 | 100 | 100 | 100 | 100 | 100 |
| Hydrogen yield | $molH_2/mol_{feed}$ | 0.18 | 0.52 | 0.60 | 0.78 | 0.58 | 0.48 | 0.80 | 0.84 | 0.82 |
| Ethanol conversion | % | 71.5 | 94.6 | 77.9 | 97.4 | 87.3 | 85.7 | 64.3 | 56.9 | 58.1 |
| Product Yields, carbon contained within category as percent of feed carbon | | | | | | | | | | |
| Acetaldehyde | | 17.5 | 16.2 | 3.0 | 6.0 | 3.3 | 22.0 | 20.5 | 14.3 | 9.4 |
| Ketone | | 4.2 | 11.9 | 9.6 | 36.3 | 7.9 | 5.1 | — | 0.9 | 0.9 |
| Acetic Acid | | 4.0 | 4.3 | 4.5 | 4.8 | 2.5 | 1.2 | 11.1 | 18.6 | 21.9 |
| Ethyl Acetate | | 18.5 | 16.9 | 45.2 | 14.5 | 31.1 | 16.2 | 21.7 | 31.1 | 20.1 |
| Diethyl Ether | | 6.5 | — | 0.02 | 0.5 | 11.1 | 3.8 | — | — | — |
| Alcohol (excluding ethanol) | | 14.5 | 15.9 | 11 | 11.4 | 24.0 | 19.4 | 1.1 | 0.6 | 0.4 |
| Olefin | | 3.0 | 3.8 | 0.1 | 0.6 | 4.5 | 2.4 | 0.1 | 0.1 | 0.1 |

Dehydrogenation and Condensation of Ethanol
Using Copper and Acidic Catalysts

The following examples illustrate a process for dehydrogenating an alkanol feed to oxygenated hydrocarbons, followed by the conversion of the oxygenates to hydrocarbons across a condensation catalyst.

A commercially available $Al_2O_3$ bound ZSM-5 support (1/16" extrudates, 20% $Al_2O_3$ Binder, ZSM-5 SAR 30, Zeolyst) was employed in these experiments.

Example 8

Nickel nitrate (Sigma Aldrich, St Louis, Mo.) was added to a commercially available $Al_2O_3$-bound ZSM-5 support (1/16" extrudates, 20% $Al_2O_3$ Binder, ZSM-5 SAR 30, Zeolyst) using excess water and evaporating the water while heating at 60° C. under vacuum and rotating in a round bottom flask until dry to achieve a target Ni loading of 1 wt %.

Example 9

Comparative Example without Dehydrogenation

An Inconel reactor with an internal diameter of 0.369 inches was loaded with the catalyst from Example 8 to a catalyst bed depth of 18 inches. The catalyst was reduced with $H_2$ at atmospheric pressure flowing at approximately 800 ml/min and the temperature was ramped from 25° C. to 370° C. in 3 hours. Once at temperature, the reactor was pressurized with $H_2$ to 100 psig and then a 70% ethanol (in DI water) mixture was fed down flow into the reactor at a WHSV of 1.9 g ethanol/g catalyst/hour. Once steady state conditions were achieved, an analysis of reaction products was completed. The gas products were analyzed by means of a gas chromatograph equipped with a flame ionization detector, the aqueous phase products were analyzed for total carbon, and the organic phase components were analyzed using a gas chromatograph equipped with both flame ionization and mass spectrometry detectors. The results obtained from this experiment are displayed in Table 6.

Example 10

An Inconel reactor with an internal diameter of 0.87 inches with an Inconel thermowell with an OD of 0.1875 inches running through the center of the reactor was loaded as a stacked bed with catalyst from Examples 4 (top catalyst, 4.25 inches) and 8 (bottom catalyst, 8.5 inches), separated by a thin layer of quartz wool. The catalyst was reduced with $H_2$ at atmospheric pressure flowing at approximately 800 ml/min and the temperature was ramped from 25° C. to 350° C. in 3 hours. Once at temperature, the reactor was pressurized with $H_2$ to 125 psig, and then a 70% ethanol (in deionized water) mixture was fed down flow into the reactor at a WHSV of 1.1 g ethanol/g ZSM-5 catalyst. Once steady state conditions were achieved, an analysis of reaction products was completed. The gas products were analyzed by means of a gas chromatograph equipped with a flame ionization detector, the aqueous phase products were analyzed for total carbon, and the organic phase components were analyzed using a gas chromatograph equipped with both flame ionization and mass spectrometry detectors. The results obtained from this experiment are displayed in Table 6.

Example 11

An Inconel reactor with an internal diameter of 0.369 inches was loaded as a stacked bed with catalyst from Examples 2 (top catalyst, 9.5 inches) and 8 (bottom catalyst, 9.5 inches), separated by a thin layer of quartz wool. The catalyst was reduced with $H_2$ at atmospheric pressure flowing at approximately 800 ml/min and the temperature was ramped from 25° C. to 370° C. in 3 hours. Once at temperature, the reactor was pressurized with $H_2$ to 100 psig, and then a 70% ethanol (in DI water) mixture was fed down flow into the reactor at a WHSV of 1.9 g ethanol/g ZSM-5 catalyst. Once steady state conditions were achieved, an analysis of reaction products was completed. The gas products were analyzed by means of a gas chromatograph equipped with a flame ionization detector, the aqueous phase products were analyzed for total carbon, and the organic phase components were analyzed using a gas chromatograph equipped with both flame ionization and mass spectrometry detectors. The results obtained from this experiment are displayed in Table 6.

Example 12

An Inconel reactor with an internal diameter of 0.87 inches was loaded with the catalyst from Example 6 to a catalyst bed depth of 8 inches. The catalyst was reduced with $H_2$ at atmospheric pressure flowing at approximately 200 ml/min, with the temperature ramped from 25° C. to 350° C. in 2 hours, then decreased to 270° C. Once at temperature, the reactor was pressurized with $H_2$ to 200 psig and then a 70% ethanol (in DI water) mixture was fed down flow into the reactor at a WHSV of 0.6 g ethanol/g catalyst/hour. The liquid product from this reactor was collected and fed across a second reactor. The second reactor was an Inconel reactor with an internal diameter of 0.369 inches loaded with the catalyst from Example 8 to a catalyst bed depth of 11 inches. The catalyst was reduced with $N_2$ at atmospheric pressure flowing at approximately 200 ml/min, with the temperature ramped from 25° C. to 370° C. in 2 hours. Once at temperature, the reactor was pressurized with $N_2$ to 100 psig and the liquid product from the first reactor was fed down flow into the reactor at a WHSV of 0.8 g non-water feed/g catalyst/hour.

Once steady state conditions were achieved, an analysis of reaction products was completed. The gas products were analyzed by means of a gas chromatograph equipped with a flame ionization detector. The aqueous phase products were analyzed for total carbon, and the organic phase components were analyzed using a gas chromatograph equipped with both flame ionization and mass spectrometry detectors. The results obtained from this experiment are displayed in Table 6.

Example 13

Three reactors were setup so that the liquid product from a first reactor would directly feed a second reactor, and all products of the second reactor would directly feed a third reactor. The first reactor is the same first reactor as described in Example 12 and operated in the manner, except for increasing the pressure to 300 psig. The second and third reactors were both Inconel reactors with an internal diameter of 0.87 inches loaded with the catalyst from Example 8 to a catalyst bed depth of 11 inches. These catalysts were reduced with $N_2$ at atmospheric pressure flowing at approximately 2300 ml/min and the temperature was ramped from 25° C. to 350° C. in 1 hour. Once at temperature, the reactors were pressurized with $N_2$ to 100 psig and the liquid product from the first reactor was fed down flow into the second reactor at a WHSV of 0.8 g non-water feed/g catalyst/hour. The third reactor was fed with the products of the second reactor at a WHSV of 0.8 g non-water feed/g catalyst/hour.

The organic phase of the third reactor was fed into a distillation column that was operating at 80 psig, a bottoms temperature of 234° C. and an overhead temperature of 108° C. At these conditions, the column was separating components lighter than toluene in the overhead of the column. All of the liquid phase produced in the overhead of the column were pumped back into the second reactor. The vapor phase products of the third reactor and distillation column were combined and a portion of the vapor stream was recycled back to the second reactor at a rate of approximately 3.2 g of vapor recycle/g non-water feed.

Once steady state conditions were achieved, an analysis of reaction products was completed. The net gas products were analyzed by means of a gas chromatograph equipped with a flame ionization detector. The aqueous phase products were analyzed for total carbon, and the organic phase components produced from the bottoms of the distillation column were analyzed using a gas chromatograph equipped with both flame ionization and mass spectrometry detectors. The results obtained from this experiment are displayed in Table 6.

Example 4. Said catalyst was loaded to a length of 8.5 inches. The top catalyst, from Example 8, was loaded to a length of 8.5 inches. The two beds of catalyst were separated by a thin layer of quartz wool and approximately 2 inches of inert packing material. Two feed lines and two HPLC pumps were installed to supply feed to both beds of catalyst. One feed line entered through the head of the reactor and the second line extended through the top bed of catalyst to bypass feed to the conversion catalyst. The entire catalyst bed was reduced at atmospheric pressure flowing at approximately 800 ml/min of $H_2$ and temperatures were ramped from 25° C. to 370° C. in 3 hours. Once at temperature, the reactor was pressurized with $H_2$ to 100 psig and then a 70% ethanol (in deionized water) mixture was fed down flow into the reactor at a WHSV of 1 g ethanol/g ZSM-5 catalyst/hour. Once steady state conditions were achieved, an analysis of reaction products was completed. The ethanol feed was split between the top and bottom in ratios of 1:1, 2:1, and 1:2 and an oxidative regeneration was performed between weight checks at each feed split ratio. The gas products were analyzed by means of a gas chromatograph equipped with a flame ionization detector, the aqueous phase products were analyzed for total carbon, and the organic phase components were analyzed using a gas chromatograph equipped with both flame ionization and mass spectroscopy detectors. The results obtained from this experiment are displayed in Table 7.

TABLE 6

Dehydrogenation and Condensation of Ethanol Using Copper and Acidic Catalysts

| Experiment | | Ex. 9 | Ex. 10 | Ex. 11 | Ex. 12 | Ex. 13 |
|---|---|---|---|---|---|---|
| Ethanol Dehydrogenation Catalyst | | None | 5% Cu on $SiO_2$ | 5% Cu on Gamma Alumina | Cu—Zn-Aluminate (Shiftmax230) | Cu—Zn-Aluminate (Shiftmax230) |
| Condensation Catalyst | | 1% Ni on $Al_2O_3$ Bound ZSM-5 | 1% Ni on $Al_2O_3$ Bound ZSM-5 | $Al_2O_3$ Bound ZSM-5 | 1% Ni on $Al_2O_3$ Bound ZSM-5 | 1% Ni on $Al_2O_3$ Bound ZSM-5 |
| Organic Phase Yield | % of feed carbon | 55 | 69 | 59 | 65 | 75 |
| Hydrogen Production | Moles of $H_2$ produced/mole of carbon fed | 0.03 | 0.42 | 0.10 | 0.24 | 0.20 |
| Total Aromatic Production | % of feed carbon | 41 | 57 | 50 | 59 | 73 |
| Total Paraffin Production | % of feed carbon | 49 | 29 | 42 | 27 | 23 |
| CO Production | % of feed carbon | 0.2 | 1.5 | 0.3 | 0.9 | 0.4 |
| $CO_2$ Production | % of feed carbon | 0.0 | 0.8 | 0.6 | 1.5 | 0.7 |
| Yield of Coke on Condensation Catalyst | % of feed carbon | Not Determined | 1.2 | Not Determined | 0.6 | 0.3 |

Example 14

An Inconel reactor with an internal diameter of 0.87 inches with an Inconel thermowell with an OD of 0.1875 inches running through the center of the reactor was loaded in a stacked bed configuration with catalyst from Examples 4 and 8. A thermowell with an OD of 0.1875 inches was placed on the centerline of the bottom bed of catalyst from Example 15

Example 14 was repeated at 300 psig. All other details specific to the experimental set-up and operation remained the same. The results obtained from this experiment are displayed in Table 7.

TABLE 7

Dehydrogenation and Condensation of Ethanol Using Copper and Acidic Catalysts

| Experiment | | Example 9 | Example 14 | | | Example 15 | | |
|---|---|---|---|---|---|---|---|---|
| Ethanol Dehydrogenation Catalyst | | None | 5% Cu on $SiO_2$ | | | 5% Cu on $SiO_2$ | | |
| Condenstation Catalyst | | 1% Ni on $Al_2O_3$ Bound ZSM-5 | 1% Ni on $Al_2O_3$ Bound ZSM-5 | | | 1% Ni on $Al_2O_3$ Bound ZSM-5 | | |
| Pressure | Psig | 100 | 100 | | | 300 | | |
| Feed Split Ratio | Dehydrogenation:Condenstation | 0:1 | 2:1 | 1:1 | 1:2 | 2:1 | 1:1 | 1:2 |
| Organic Phase Yield | % of feed carbon | 55 | 60 | 56 | 57 | 62 | 53 | 58 |
| Hydrogen Production | Moles of $H_2$ produced/mole of carbon fed | 0.03 | 0.19 | 0.13 | 0.08 | 0.11 | 0.09 | 0.06 |
| Total Aromatic Production | % of feed carbon | 41 | 57 | 52 | 49 | 51 | 45 | 43 |
| Total Paraffin Production | % of feed carbon | 49 | 39 | 39 | 42 | 38 | 48 | 46 |

The invention claimed is:

1. A method of converting a mixture of oxygenates to aromatic hydrocarbons, the method comprising:
providing a first oxygenate, the first oxygenate comprising a $C_1$-$C_6$ alkanol;
providing a second oxygenate, the second oxygenate comprising a carboxylic acid, an aldehyde, an ester, or any combination thereof, wherein the second oxygenate has a hydrogen to carbon effective ratio of less than 1.6;
producing a mixture of oxygenates, the mixture of oxygenates comprising at least the first oxygenate and the second oxygenate, wherein the mixture of oxygenates has a total hydrogen to carbon effective ratio of between 1.2 and 1.6; and
exposing the mixture of oxygenates to an oxygenate conversion catalyst at an oxygenate conversion temperature and an oxygenate conversion pressure to produce aromatic hydrocarbons.

2. The method of claim 1, wherein the second oxygenate is produced by dehydrogenation of a portion of the first oxygenate.

3. The method of claim 1, the method further comprising:
separating the first oxygenate to form a first portion of the first oxygenate and a second portion of the first oxygenate; and
exposing the first portion of the first oxygenate to a dehydrogenation catalyst at an effective temperature and an effective pressure to produce the second oxygenate,
wherein the mixture of oxygenates is produced by mixing the second portion of the first oxygenate and the second oxygenate.

4. The method of claim 1, wherein the mixture of oxygenate components comprises the carboxylic acid and wherein the carboxylic acid has a hydrogen to carbon effective ratio less than 1.6.

5. The method of claim 4, wherein the carboxylic acid is acetic acid.

6. The method of claim 1, wherein the mixture of oxygenate components comprises the ester and wherein the ester has a hydrogen to carbon effective ratio less than 1.6.

7. The method of claim 6, wherein ester is ethyl acetate.

8. The method of claim 1, wherein the mixture of oxygenate components comprises the aldehyde and wherein aldehyde has a hydrogen to carbon effective ratio is less than 1.6.

9. The method of claim 8, wherein the aldehyde is acetaladehyde.

10. The method of claim 1, wherein the mixture of oxygenate components comprises the carboxylic acid, the aldehyde, and the ester and wherein the carboxylic acid, the aldehyde, and the ester have a hydrogen to carbon effective ratio of less than 1.6.

11. The method of claim 10, wherein the carboxylic acid comprises acetic acid, the aldehyde comprises acetaladehyde, and the ester comprises ethyl acetate.

12. The method of claim 1, wherein the mixture of oxygenates further comprises a ketone, an ether, or combinations thereof.

13. The method of claim 1, wherein the $C_1$-$C_6$ alkanol comprises two or more $C_1$-$C_6$ alkanols.

14. The method of claim 1, wherein the $C_1$-$C_6$ alkanol comprises methanol, ethanol, propanol, butanol, or combinations thereof.

15. The method of claim 1, wherein the $C_1$-$C_6$ alkanol comprises ethanol.

16. The method of claim 1, wherein the total hydrogen to carbon effective ratio is less than 1.5.

17. The method of claim 3, wherein the dehydrogenation catalyst comprises:
(i) a metal selected from the group consisting of Cu, Ru, Ag, CuCr, CuZn, Co, Raney copper, copper-zinc-aluminate, alloys thereof, and combinations thereof; and/or
(ii) a support selected from the group consisting of alumina, silica, silica-alumina, titania, carbon, zirconia, zinc aluminate, and mixtures thereof.

18. The method of claim 3, wherein:
(i) the dehydrogenation temperature is between about 80° C. and 500° C.; and/or
(ii) the dehydrogenation pressure ranges from below atmospheric pressure to about 1000 psig.

19. The method of claim 1, wherein the oxygenate conversion catalyst comprises a zeolite.

20. The method of claim 19, wherein the oxygenate conversion catalyst:
(i) is ZSM-5;
(ii) is modified by a material selected from the group consisting of phosphorous, gallium, zinc, nickel, tungsten, and mixtures thereof; and/or (iii) contains a binder selected from the group consisting of alumina, silica, silica-alumina, titania, zirconia, aluminum phosphate, and mixtures thereof.

21. The method of claim 1, wherein:
(i) the oxygenate conversion temperature is between about 250° C. and 550° C.; and/or
(ii) the oxygenate conversion pressure ranges from less than atmospheric pressure to about 1000 psig.

* * * * *

UNITED STATES PATENT AND TRADEMARK OFFICE
CERTIFICATE OF CORRECTION

PATENT NO. : 9,873,643 B2  
APPLICATION NO. : 14/583312  
DATED : January 23, 2018  
INVENTOR(S) : Paul G. Blommel et al.

Page 1 of 1

It is certified that error appears in the above-identified patent and that said Letters Patent is hereby corrected as shown below:

In the Specification

Column 8, Line 8, "HA" should be -- IIA --

Signed and Sealed this  
Thirtieth Day of July, 2019

Andrei Iancu  
*Director of the United States Patent and Trademark Office*